(12) United States Patent
Roche

(10) Patent No.: US 10,233,477 B2
(45) Date of Patent: Mar. 19, 2019

(54) CULTURE MEDIUM FOR MICROORGANISMS INCLUDING PARA-AMINOBENZOIC ACID AS A SELECTIVE AGENT

(75) Inventor: Jean-Marc Roche, Feisson sur Salins (FR)

(73) Assignee: BIOMERIEUX, Marcy l'etoile (FR)

( * ) Notice: Subject to any disclaimer, the term of this patent is extended or adjusted under 35 U.S.C. 154(b) by 90 days.

(21) Appl. No.: 13/978,590

(22) PCT Filed: Jan. 31, 2012

(86) PCT No.: PCT/FR2012/050207
§ 371 (c)(1),
(2), (4) Date: Jul. 8, 2013

(87) PCT Pub. No.: WO2012/104544
PCT Pub. Date: Aug. 9, 2012

(65) Prior Publication Data
US 2013/0280756 A1    Oct. 24, 2013

(30) Foreign Application Priority Data
Feb. 1, 2011 (FR) .................... 11 50768

(51) Int. Cl.
*C12Q 1/04* (2006.01)
*C12Q 1/02* (2006.01)
*C12Q 1/10* (2006.01)
*C07C 229/52* (2006.01)

(52) U.S. Cl.
CPC .............. *C12Q 1/04* (2013.01); *C12Q 1/02* (2013.01); *C12Q 1/045* (2013.01); *C12Q 1/10* (2013.01); *C07C 229/52* (2013.01); *G01N 2333/255* (2013.01)

(58) Field of Classification Search
CPC . C12Q 1/04; C12Q 1/045; C12Q 1/10; C12Q 1/00
See application file for complete search history.

(56) References Cited

U.S. PATENT DOCUMENTS

| | | | |
|---|---|---|---|
| 4,279,995 A * | 7/1981 | Woods et al. | 435/38 |
| 5,786,167 A | 7/1998 | Tuompo et al. | |
| 6,037,140 A * | 3/2000 | Carles et al. | 435/30 |
| 2008/0182272 A1 * | 7/2008 | Nagar et al. | 435/7.2 |

FOREIGN PATENT DOCUMENTS

| | | |
|---|---|---|
| EP | 1 325 024 | 7/2003 |
| EP | 1 334 175 | 8/2003 |
| WO | WO 96/30543 | 10/1996 |
| WO | WO 96/40980 | 12/1996 |
| WO | WO 98/04674 | 2/1998 |
| WO | WO 01/66790 | 9/2001 |
| WO | WO 02/22785 | 3/2002 |
| WO | WO 02/24725 | 3/2002 |

OTHER PUBLICATIONS

Wood-2 et al., British journal of experimental pathology, 21(2): 74-90, 1940.*
Eagon et al., Journal of Antimicrobial Chemotheraphy, 25: 25-29, 1990.*
M. Manafi, International Journal of Food Microbiology, 60:205-218, 2000.*
Johnson et al., Journal of AOAC International, 92(6) 1861-1864, published in Nov. 2009.*
R. M. E. Richards et al., "Activity of p-arninobenzoic acid compared with other organic acids against selected bacteria," Journal of Applied Bacteriology, vol. 78, 1995, pp. 209-215.
Written Opinion dated May 21, 2012 issued in International Patent Application No. PCT/FR2012/050207.
Xie, "Improving Selenite Cystine Culture Medium to Increase the Detection of Carriers of *Salmonella* genus," Chinese Journal of Health Laboratory Technology, vol. 5, No. 5, p. 306, 1995 (with translation).

* cited by examiner

*Primary Examiner* — Jennifer Pitrak McDonald
*Assistant Examiner* — Qing Xu
(74) *Attorney, Agent, or Firm* — Oliff PLC

(57) ABSTRACT

The field of the invention is the analysis of target microorganisms in a complex sample. The present invention more particularly relates to a culture medium for the detection of at least one target microorganism including: at least one natural or synthetic fermentation or enzymatic activity substrate, and at least one selective agent, which inhibits non-target microorganisms, constituted by para-amino benzoic acid, one of its derivatives or one of their salts, at a concentration of between 0.05 and 1 g/L.

14 Claims, No Drawings

CULTURE MEDIUM FOR MICROORGANISMS INCLUDING PARA-AMINOBENZOIC ACID AS A SELECTIVE AGENT

The field of the invention is the analysis of target microorganisms in a complex sample.

More particularly, the present invention relates to the detection of microorganisms such as *Salmonella* bacteria, by means of a culture medium containing para-aminobenzoic acid as a selective agent.

The quality and the safety of marketed products are among the major concerns in the agri-food industry across the globe. In the raw materials and in the finished products, it must be possible to detect, identify and quantify the microbial flora, and thus to guarantee the value of the products, from their manufacture to their consumption. It is important to distinguish on the one hand the product's quality indicators, which reflect an overall rate of contamination by a spoilage flora, among which are enterobacteria such as *Escherichia coli*, coagulase-positive staphylococci, *Pseudomonas, Bacilli*, yeasts, mildews, etc., and on the other hand the detection of pathogens such as *Salmonella* or *Listeria monocytogenes*. Microbiological analysis is therefore vital in terms of public health and in economic terms for this industry.

The development of tests for detecting target microorganisms in a sample meets strict constraints and makes it necessary to find a compromise between sensitivity, defined as the ability to reveal the sought species, when a small quantity of it is present in a sample to be tested, and selectivity, defined as the ability to detect the sought species in the sample which also contains other species. The combination of the components which ensure sensitivity with those which ensure the selectivity makes it possible to obtain a specific test.

The sensitivity criterion frequently makes it necessary to employ a composition for culturing the target microorganisms, in order to make them detectable. The specificity can thus be provided by incorporating into the culture medium a labelling molecule involved in the metabolism of the target microorganisms; this interaction produces a measurable signal.

On the other hand, depending on whether it is desired to detect and count a specific genus or the total viable germs, a selective medium may or may not be used.

If target microorganisms are sought, in particular bacteria, the use of chromogenic culture media is increasingly important. The advantage of such media is that they contain enzyme substrates specifically cleaved or digested by the target bacteria, such that a coloured reaction product is generated, which remains generally localised in the colonies of said bacteria. This makes it possible to differentiate said target bacteria from the other bacteria genera potentially present in the sample, in particular in the case of an agri-food sample. Such culture media also make it possible to identify a bacterial species contained in a clinical sample, this species generally being the source of an infection.

In the case of seeking pathogenic target microorganisms in agri-food samples, it would generally appear that the target microorganism is present in the mixed population of microorganisms in much lower quantity than the non-target microorganisms. Besides simply differentiating the target microorganism from the non-target microorganisms, there is also the need to selectively inhibit the growth of said non-target microorganisms, in order to be able to detect the target microorganism, without which the development of said non-target microorganisms would tend to mask the target microorganism, even if the colonies of this latter are coloured, and thus lead to false-negative results.

In particular, it is necessary to be able to differentiate the *Salmonella* genus bacteria from other bacterial types, particularly gram-negative bacteria, such as bacteria of the *Escherichia coli* (*E. coli*) species, which are amongst the commensal bacteria present in the samples.

To this end, document WO-A-96/30543 describes a culture medium for the detection of *Salmonella*, including a chromogenic substrate for the β-galactosidase positive enterobacter species such as *E. coli* and a mixture of sugars metabolised by *Salmonella*, generating an acidic compound and a pH indicator which reveals the acidification of the medium. Furthermore, bile salts are present in the medium to selectively inhibit the gram-positive species.

An alternative method for specifically detecting *Salmonella* genus bacteria and differentiating gram-negative bacteria has been described in the documents EP-B-1 334 175 and EP-A-1 325 024. This method consists in using, in a culture medium, a selective agent in the form of a so-called "suicide" substrate. Such a substrate is in fact made up of a so-called "transporter" part and a so-called "toxic" part, these parts being linked to one another by a bond intended to be broken by *E. coli* bacteria and not by *Salmonella*, which causes the release and concentration of the toxic part inside *E. coli* and thus inhibits its growth, in favour of that of *Salmonella*. The suicide substrate of choice is alafosfalin.

A main disadvantage of such a substrate is that it competes with the amino acids present in the culture medium. Also, for it to be active on a large number of bacterial species, it is necessary to have a culture medium which is relatively low in amino acids, which does not promote the growth of *Salmonella* genus bacteria. Furthermore, alafosfalin is a relatively costly compound, which greatly burdens the price of the medium.

The present invention remedies these disadvantages by proposing a solution consisting in a culture medium comprising para-amino benzoic acid as a selective agent. A culture medium is defined here as a medium including all the elements necessary for the survival and/or the growth of microorganisms, namely amino acids or protein hydrolysates, minerals, vitamins and generally all of the nutrients and metabolic sources known to the person skilled in the art for enabling microbial growth.

The inventors have indeed demonstrated, rather surprisingly, that the addition of para-amino benzoic acid at a relatively high concentration, into a suitable culture medium, inhibits or slows in particular the growth of gram-negative bacteria, such as enterobacteria, in favour of *Salmonella* genus bacteria.

More particularly, the invention relates to a culture medium for microorganisms including:
  at least one natural or synthetic fermentation or enzymatic activity substrate, and
  at least one selective agent, constituted by para-amino benzoic acid, one of its derivatives or one of their salts, at a concentration of between 0.05 and 1 g/L, preferably between 0.05 and 0.8 g/L.

Preferably, the target microorganism is a *Salmonella* genus bacterium.

The non-target microorganisms are from the group of gram-negative bacteria notably including enterobacteria.

A para-amino benzoic acid derivative can be from the group notably including 4-aminobenzoic acid, 4-(methylamino) benzoic acid, 4-amino-2-chlorobenzoic acid, 4-amino-3-nitro benzoic acid, 4-aminosalicylic acid.

An acceptable salt can be, for example, a potassium salt or a sodium salt. Potassium 4-aminobenzoate or sodium 4-aminobenzoate can thus be used as a compound.

Advantageously, the culture medium according to the invention comprises at least one chromogenic or fluorogenic enzyme substrate.

Preferably, the culture medium according to the invention further comprises bile salts. It can include sodium deoxycholate, for example.

Advantageously, said culture medium can comprise at least one other selective agent from the group including: Novobiocin, Vancomycin, Amphotericin, Cefsulodin.

Within the terms of the present invention, the substrate is chosen from any substrate able to be hydrolysed into a product which makes it possible to detect, directly or indirectly, an enzymatic activity specific to the microorganism sought. In the case of direct detection, the substrate includes a first part specific to the enzymatic activity and a second part which acts as a label, which can be chromogenic or fluorescent.

The substrate can likewise be a metabolic substrate, such as a carbon or nitrogen source, the degradation product of which varies the pH, this variation being detectable by means of a pH indicator. The pH indicator is a chemical substance whose colour varies depending on pH changes linked to microbial growth. As examples of pH indicator, mention can be made of neutral red, aniline blue, bromocresol blue. In a second embodiment, the pH indicator is a fluorophore (for example 4-methylumbelliferone, coumarin or resorufin derivatives).

Within the terms of the invention, selective agent is understood to mean any compound likely to promote the growth of a target microorganism and/or inhibit the growth of a non-target microorganism or microorganisms.

The culture medium which is the subject of the invention can be in powder form, gel form or liquid form, ready-to-use, i.e. ready to be seeded in a tube, flask or on a Petri dish. In the case of a gelled medium, agar is the conventional gelling agent in microbiology for culturing of microorganisms, but it is possible to use another gelling agent, such as, for example, gelatine or agarose. Finally, the medium can be packaged in a bottle, a cartridge or a card specific to an automated bacteriology device. By way of example, mention can be made of the Vitek® card, Tempo® card and the BacT/ALERT® bottle marketed by the applicant.

The invention also relates to a process for detecting a target microorganism in a mixed population of target and non-target cells, including the steps consisting of:
- placing a sample, in which it is desired to reveal said target microorganisms, in contact with a culture medium according to the invention,
- incubating the entirety at a temperature which promotes the reproduction of said microorganisms,
- observing the microorganisms on said culture medium.

The temperature promoting the growth of microorganisms is between 20 and 44° C., and the sample is kept at this temperature for a duration sufficient to allow the detection of the microorganisms, namely a duration of between 2 and 96 hours. With regard to the incubation atmosphere, it is preferably aerobic, but it can also be anaerobic or in $CO_2$. Identification can be made by the naked eye by viewing a change in coloration which does not spread into the culture medium, i.e. is concentrated in the colonies. If fluorescence is revealed, the fluorescence-reading devices known to the person skilled in the art are used.

The culture medium and the detection method which are subjects of the invention are used for samples of food, environmental or clinical origin. The sample is defined as an isolated small part or small quantity of an entity for analysis.

Among the samples of food origin, mention can be made, in a non-exhaustive manner, of a sample of dairy products (yoghurts, cheeses, etc.), meat, fish, eggs, fruits, vegetables, water, beverages (milk, fruit juice, soda, etc.). Finally, a food sample can be from an animal feed, such as notably animal meals.

Mention can also be made of environmental samples such as surface, water and air specimens.

Samples of clinical origin can correspond to specimens of whole blood, serum, plasma, urine, faeces, cerebrospinal fluid, specimens of nose, throat, skin, wounds, organs, tissue or isolated cells, etc.

The invention finally relates to the in vitro use of para-aminobenzoic acid, one of its derivatives or one of their salts, as a selective agent. Advantageously, it is used at a concentration of between 0.05 and 1 g/L, preferably between 0.05 and 0.8 g/L The following examples are given by way of illustration and are by no means limiting. They make it possible to better understand the invention.

EXAMPLES

Example 1—Culture Medium for the Detection of *Salmonella* Genus Bacteria Including 3 Chromogenic Substrates, a Combination of Antibiotics (Novobiocin, Cefsulodin, Vancomycin, Amphotericin) and Different Concentrations of Para-Aminobenzoic Acid (PABA)

1. Preparation of the Tested Media
The tested media are as follows:
Control medium: chromID® *Salmonella* medium (ref. 43621) marketed by the applicant, containing Novobiocin, Vancomycin, Amphotericin and Cefsulodin and the three chromogenic substrates
Medium 1: Control medium, with addition of 0.1 g/L PABA,
Medium 2: Control medium, with addition of 0.3 g/L PABA,
Medium 3: Control medium, without antibiotics and with addition of 0.5 g/L PABA,
These media are media in 90-millimeter Petri dishes.

2. Seeding and Reading of the Media
Strains of different *Salmonella* species or serovars (*S. enteritidis, S. thyphimurium, S. cabana, S. gallinarum, S. paratyphi* for example) and other microbe genera such as the gram-negative bacteria (*E. coli, Enterobacter, Citrobacter, Proteus, Hafnia*), all from the Applicant's collection, were suspended in physiological water, then seeded on the media, in accordance with the 4-quadrant technique. The strains were incubated at 37° C. for 24 hours. The colonies formed were examined visually after 24 hours of incubation.

3. Results:
The results obtained are presented in table 1 below.

TABLE 1

| Medium | *Salmonella* detected/*Salmonella* tested | Gram strains - other than *Salmonella* with growth/Gram strains - other than *Salmonella* tested |
|---|---|---|
| Control | 9/9 | 8/10 |
| 1 | 9/9 | 6/10 |

TABLE 1-continued

| Medium | Salmonella detected/Salmonella tested | Gram strains - other than Salmonella with growth/Gram strains - other than Salmonella tested |
|---|---|---|
| 2 | 9/9 | 7/10 |
| 3 | 9/9 | 1/5 |

These results show a good degree of sensitivity of detection of the *Salmonella* strains by all of the culture media. However, only media 1 to 3 decrease the growth of other Gram-negative bacteria.

Example 2—Culture Medium for the Detection of *Salmonella* Genus Bacteria Including 3 Chromogenic Substrates, a Combination of Selective Elements (Novobiocin, Cefsulodin, Vancomycin, Amphotericin, Bile Salts, Sodium Deoxycholate) and Para-Aminobenzoic Acid (PABA)

1. Preparation of the Medium According to the Invention
The media tested in the experiments were as follows:
Control Medium: chromID® *Salmonella* medium (ref. 43621) containing Novobiocin, Vancomycin, Amphotericin, Cefsulodin, 1.5 g/L bile salts and 3 chromogenic substrates
Medium 1: Control medium, with addition of 0.1 g/L PABA, bile salts increased to 3 g/L
Medium 2: Control medium, with addition of 0.1 g/L PABA, bile salts increased to 3 g/L and 5 g/L sodium deoxycholate 2. Seeding and Reading of the Media
Strains belonging to different species or serovars of *Salmonella* (*S. enteritidis, S. thyphimurium, S. cubana, S. gallinarum, S. paratyphi, S. arizonae* for example) and other microbe genera, such as the gram-negative bacteria (*Serratia, Enterobacter, Citrobacter, Proteus, Hafnia*) all from the Applicant's collection, were suspended in physiological water, then seeded on the media, in accordance with the 4-quadrant technique. The dishes were incubated at 37° C. for 24 hours. The colonies formed were examined visually after 24 hours of incubation.

3. Results:
The results obtained are presented in table 2 below.

TABLE 2

| Medium | Salmonella detected/Salmonella tested | Bacteria genera other than Salmonella with growth/other bacteria genera tested |
|---|---|---|
| C | 9/10 | 5/6 |
| 1 | 9/10 | 3/6 |
| 2 | 10/10 | 1/6 |

These results show an excellent degree of sensitivity of all of the media for seeking *Salmonella* strains, with detection of all of the 10 *Salmonella* strains for formula 2.
However, only media 1 and 2 make it possible to decrease the growth of bacteria genera other than *Salmonella*. The best selectivity is obtained by associating PABA with bile salts such as sodium deoxycholate.

The invention claimed is:
1. A culture medium for the detection of at least one target microorganism comprising:
at least one natural or synthetic fermentation or enzymatic substrate of the at least one target microorganism; and
selective agents, wherein the selective agents consist of:
bile salts,
at least one agent selected from the group consisting of para-amino benzoic acid, a derivative of para-amino benzoic acid, a salt thereof, and combinations thereof, and
optionally at least one of Novobiocin, Vancomycin, Amphotericin, and Cefsulodin;
wherein a concentration of the para-amino benzoic acid, a derivative of para-amino benzoic acid, and/or a salt thereof ranges from 0.05 to 1 g/L;
the derivative of para-amino benzoic acid comprises a para-amino benzoic skeleton;
the at least one target microorganism is a *Salmonella* genus bacterium;
the at least one natural or synthetic fermentation or enzymatic substrate comprises at least one chromogenic or fluorogenic substrate; and
a hydrolysation of the at least one natural or synthetic fermentation or enzymatic substrate distinguishes the at least one target microorganism from non-target microorganisms in the culture medium by causing a change in color or fluorescence, respectively, in the target microorganism.

2. The culture medium according to claim 1, wherein the culture medium contains at least one component that promotes a culturing of the *Salmonella* genus bacterium.

3. The culture medium according to claim 1, wherein the non-target microorganisms are selected from the group consisting of enterobacteria, except a *Salmonella* genus bacterium, and the culture medium contains at least one component that inhibits or slows a culturing of the non-target microorganisms.

4. The culture medium according to claim 1, wherein the derivative of para-amino benzoic acid is selected from the group consisting of 4-(methylamino) benzoic acid, 4-amino-2-chlorobenzoic acid, 4-amino-3-nitro benzoic acid, and 4-aminosalicylic acid.

5. The culture medium according to claim 1, wherein the bile salts comprise at least sodium deoxycholate.

6. The culture medium according to claim 1, wherein the selective agents include the at least one of Novobiocin, Vancomycin, Amphotericin, and Cefsulodin.

7. The culture medium according to claim 1, wherein the at least one natural or synthetic fermentation or enzymatic substrate is a metabolic substrate.

8. The culture medium according to claim 7, wherein a degradation product of the metabolic substrate varies a pH of the culture medium.

9. The culture medium according to claim 1, wherein the concentration of the para-amino benzoic acid, a derivative of para amino benzoic acid, and/or a salt thereof ranges from 0.3 to 1 g/L.

10. The culture medium according to claim 1, wherein the concentration of the para-amino benzoic acid, a derivative of para-amino benzoic acid, and/or a salt thereof ranges from 0.5 to 1 g/L.

11. A culture medium for the detection of at least one target microorganism comprising:
at least three chromogenic substrates; and
selective agents, wherein the selective agents consist of:
bile salts, at least one agent selected from the group consisting of para-amino benzoic acid, a derivative of para-amino benzoic acid, a salt thereof, and combinations thereof, and optionally at least one of Novobiocin, Vancomycin, Amphotericin, and Cefsulodin;

wherein a concentration of the at least one agent ranges from 0.05 to 1 g/L;

the derivative of para-amino benzoic acid comprises a para-amino benzoic skeleton;

the at least one target microorganism is a *Salmonella* genus bacterium; and a hydrolysation of one or more of the at least three chromogenic substrates distinguishes the at least one target microorganism from non-target microorganisms in the culture medium by causing a change in color in the target microorganism.

12. A process for detecting a target microorganism, in a mixed population of target and non-target microorganisms, comprising:

placing a sample, in which it is desired to detect the target microorganism in the sample, in contact with the culture medium according to claim 1;

incubating the culture medium at a temperature that promotes reproduction of the target microorganism; and observing the microorganisms on the culture medium, wherein the target microorganism is a *Salmonella* genus bacterium.

13. A method comprising: detecting in vitro at least one target microorganism with the culture medium according to claim 1, wherein the at least one target microorganism is a *Salmonella* genus bacterium.

14. A method comprising:

detecting at least one target microorganism with the culture medium of claim 1.

* * * * *